US00RE44214E

(19) United States
(12) Reissued Patent
Peterson et al.

(10) Patent Number: US RE44,214 E
(45) Date of Reissued Patent: May 14, 2013

(54) UNMANNED INTEGRATED OPTICAL REMOTE EMISSIONS SENSOR (RES) FOR MOTOR VEHICLES

(75) Inventors: Jay Peterson, Montecito, CA (US); David R Nelson, Santa Barbara, CA (US); Troy P. Bahan, Santa Barbara, CA (US); George C. Polchin, Santa Barbara, CA (US); Michael D. Jack, Goleta, CA (US)

(73) Assignee: Envirotest Systems Holdings Corp., East Granby, CT (US)

(21) Appl. No.: 12/489,349

(22) Filed: Jun. 22, 2009
(Under 37 CFR 1.47)

Related U.S. Patent Documents

Reissue of:
(64) Patent No.: 5,726,450
Issued: Mar. 10, 1998
Appl. No.: 08/739,487
Filed: Oct. 26, 1996

U.S. Applications:
(60) Division of application No. 09/708,713, filed on Nov. 9, 2000, now Pat. No. Re. 40,767, which is a continuation of application No. 09/521,858, filed on Mar. 9, 2000, now abandoned.

(51) Int. Cl.
*G01N 21/00* (2006.01)
*G01N 21/35* (2006.01)
*G01N 21/25* (2006.01)

(52) U.S. Cl.
USPC ..... 250/338.5; 250/339.13; 250/252.1; 356/436

(58) Field of Classification Search ..... 250/338.5, 250/339.13
See application file for complete search history.

(56) References Cited

U.S. PATENT DOCUMENTS 3,593,023 A 7/1971 Dodson et al.
3,696,247 A 10/1972 McIntosh et al.
3,743,426 A 7/1973 Steinberg (Continued)

OTHER PUBLICATIONS

"Remote Sensing Enhanced Motor Vehicle Emissions Control for Pollution Reduction in the Chicago Metropolitan Area: Sitting and Issue Analysis", IL Dept. of Energy and Natural Resources, ILENR/RE-AQ-91/15, Oct. 1991.

(Continued)

*Primary Examiner* — Marcus Taningco
(74) *Attorney, Agent, or Firm* — Pillsbury Winthrop Shaw Pittman LLP

(57) ABSTRACT

An unmanned integrated RES 12 integrates all of its components except the reflector 22 into a single console 30 that is positioned at the side of a road and has a CPU 36 that controls calibration, verification and data gathering. The RES's source 32 and receiver 34 are preferably stacked one on top of the other such that the IR beam 24 traverses a low and high path as it crosses the road 14. This allows the RES to detect both low and high ground clearance vehicles. To maintain the vehicle processing and identification throughput, the speed sensor 54 and ALPR 48,50 detect the passing vehicles at steep angles, approximately 20 to 35 degrees. In a preferred system, a manned control center 16 communicates with a large number of the unmanned integrated RES to download emissions data, perform remote diagnostics, and, if necessary, dispatch a technician to perform maintenance on a particular RES.

7 Claims, 7 Drawing Sheets

U.S. PATENT DOCUMENTS

| | | | | | |
|---|---|---|---|---|---|
| 3,908,167 | A | | 9/1975 | Hulls et al. | |
| 3,957,372 | A | | 5/1976 | Jowett et al. | |
| 3,958,122 | A | | 5/1976 | Jowett et al. | |
| 3,973,848 | A | | 8/1976 | Jowett et al. | |
| 4,160,373 | A | | 7/1979 | Fastaia et al. | |
| 4,390,785 | A | | 6/1983 | Faulhaber et al. | |
| 4,480,191 | A | | 10/1984 | Karpowycz | |
| 4,490,043 | A | | 12/1984 | Cramp | |
| 4,516,858 | A | * | 5/1985 | Gelbwachs | 356/437 |
| 4,544,273 | A | | 10/1985 | Berndt | |
| 4,560,873 | A | | 12/1985 | McGowan et al. | |
| 4,632,563 | A | | 12/1986 | Lord, III | |
| 4,663,961 | A | | 5/1987 | Nelson et al. | |
| 4,678,914 | A | | 7/1987 | Melrose et al. | |
| 4,719,360 | A | | 1/1988 | Kontani et al. | |
| 4,746,218 | A | | 5/1988 | Lord, III | |
| 4,765,961 | A | | 8/1988 | Schiff et al. | |
| 4,795,253 | A | | 1/1989 | Sandridge et al. | |
| 4,810,884 | A | | 3/1989 | Carlson | |
| 4,818,705 | A | | 4/1989 | Schneider et al. | |
| 4,829,183 | A | | 5/1989 | McClatchie et al. | |
| 4,924,095 | A | | 5/1990 | Swanson, Jr. | |
| 4,990,780 | A | | 2/1991 | Lee et al. | |
| 4,999,498 | A | | 3/1991 | Hunt et al. | |
| 5,060,505 | A | | 10/1991 | Tury et al. | |
| 5,099,680 | A | | 3/1992 | Fournier et al. | |
| 5,105,651 | A | | 4/1992 | Gutmann | |
| 5,129,257 | A | | 7/1992 | Carduner et al. | |
| 5,184,017 | A | | 2/1993 | Tury et al. | |
| 5,210,702 | A | | 5/1993 | Bishop et al. | |
| 5,246,868 | A | | 9/1993 | Busch et al. | |
| 5,252,828 | A | | 10/1993 | Kert et al. | |
| 5,306,913 | A | | 4/1994 | Noack et al. | |
| 5,319,199 | A | | 6/1994 | Stedman et al. | |
| 5,332,901 | A | | 7/1994 | Eckles et al. | |
| 5,343,043 | A | | 8/1994 | Johnson | |
| 5,371,367 | A | | 12/1994 | DiDomenico et al. | |
| 5,373,160 | A | | 12/1994 | Taylor | |
| 5,386,373 | A | | 1/1995 | Keeler et al. | |
| 5,401,967 | A | | 3/1995 | Stedman et al. | |
| 5,418,366 | A | | 5/1995 | Rubin et al. | |
| 5,442,553 | A | * | 8/1995 | Parrillo | 455/420 |
| 5,451,787 | A | | 9/1995 | Taylor | |
| 5,489,777 | A | | 2/1996 | Stedman et al. | |
| 5,498,872 | A | | 3/1996 | Stedman et al. | |
| 5,568,121 | A | * | 10/1996 | Lamensdorf | 340/539.17 |
| 5,572,424 | A | | 11/1996 | Kellogg et al. | |
| 5,583,765 | A | | 12/1996 | Kleehammer | |
| 5,589,629 | A | | 12/1996 | Quinn | |
| 5,591,975 | A | | 1/1997 | Jack et al. | |
| 5,621,166 | A | | 4/1997 | Butler | |
| 5,644,133 | A | | 7/1997 | Didomenico et al. | |
| 5,693,872 | A | | 12/1997 | Quinn | |
| 5,719,396 | A | | 2/1998 | Jack et al. | |
| 5,726,450 | A | | 3/1998 | Peterson et al. | |
| 5,731,510 | A | | 3/1998 | Jones et al. | |
| 5,753,185 | A | | 5/1998 | Mathews et al. | |
| 5,831,267 | A | | 11/1998 | Jack et al. | |

OTHER PUBLICATIONS

Bishop, Gary A., et al., "Oxygenated Fuels, A Remote Sensing Evaluation", *SAE Technical Paper Series,* May 1989.

Bishop, Gary A., et al., "IR Long-Path Photometry: A Remote Sensing Tool for Automobile Emissions," American Chemical Society, May 1989.

Technical Proposal—"Vehicle Inspection Instrumentation"; submitted to California Air Resources Board; Sep. 1, 1971, Lockheed Palo Alto Research Laboratory, Lockheed Missiles & Space Company—A Group Division of Lockheed Aircraft Corporation, Palo Alto, California.

Hoshizaki, et al., Final Report—"Vehicle Inspection Instrumentation"; submitted to California Air Resources Board; Jun. 1973, Lockheed Palo Alto Research Laboratory, Lockheed Missiles & Space Company—A Group Division of Lockheed Aircraft Corporation, Palo Alto, California.

http://www.epa.gov/otaq/15-remot.htm; "Remote Sensing: A Supplemental Tool for Vehicle Emission Control," Aug. 1993, EPA 400-F-92-017, Fact Sheet OMS-15; 4 pages.

Lucien W. Chaney, "The Remote Measurement of Traffic Generated Carbon Monoxide, APCA Note-Book," Journal of the Air Pollution Association; Copyright 1983; 3 pages.

Paul Stockwell, "Tunable Diode Laser Systems Break New Ground in Water Vapour Analysis"; IMA Ltd., Unit Newall Hall Park, Otley, West Yorkshire, United Kingdom; [undated]; 8 pages.

Mark G. Allen, "Diode Laser Absorption Sensors for Gas Dynamic and Combustion Flows," Copyright 1998 Measurement Science and Technology 9; 61 pages.

Kerry L. Swayne, "Infrared Remote Sensing of On-Road Motor Vehicle Emissions in Washington State," Mar. 1999, Air Quality Program, Washington State Department of Ecology, Washington; Publication #99-204; 20 pages.

Robert D. Stephens, "Remote Sensing Data and a Potential Model of Vehicle Exhaust Emissions," Nov. 1994, vol. 44, Journal of Air & Waste Management Association, pp. 1284-1292.

"An Analysis of On-Road Remote Sensing as a Tool for Automobile Emissions Control," Final Report Prepared by University of Denver Chemistry Department, Colorado, Mar. 1990; 174 pages; prepared for Illinois Department of Energy and Natural Resources.

Robert D. Stephens, et al., "Remote Sensing Measurements of In-Use Vehicle Carbon Monoxide and Hydrocarbon Exhaust Emissions," Environmental Science Department, Michigan, to be presented to Society of Automotive Engineers Government/Industry Meeting, Washington, D.C., May 15, 1991; 9 pages.

Thomas C. Austin, et al., "An Evaluation of "Remote Sensing" for the Measurement of Vehicle Emissions," prepared for The California Air Resources Board and The California I/M Review Committee, Aug. 28, 1990, 30 pages; prepared by Sierra Research, Inc., California.

Robert D. Stephens, et al., "Remote Sensing Measurements of Carbon Monoxide Emissions from On-Road Vehicles," Copyright Jan. 1991, Air & Waste Management Association, vol. 42, No. 1, pp. 39-46.

Donald H. Stedman, et al., "Remote Sensing of On-Road Vehicle Emissions," Final Report to Coordinating Research Council, The University of Denver, Jan. 6, 1992, 21 pages.

Peter Popp, et al., "Development of a High-Speed Ultraviolet Spectrophotometer Capable of Real-Time NO and Aromatic Hydrocarbon Detection in Vehicle Exhaust," Department of Chemistry, University of Denver, Colorado, Prepared for Proceedings of the 7$^{th}$ CRC On-Road Vehicle Emissions Workshop, San Diego, California, Apr. 9-11, 1997; 10 pages.

John DiDomenico, et al., "Preliminary Results from Cold Start Sensor Testing," Presented to 7$^{th}$ CRC On-Road Vehicle Emissions Workshop, San Diego, California Apr. 9-11, 1997; 1 page.

Gary A. Bishop, et al., "Enhancements of Remote Sensing for Vehicle Emissions in Tunnels," Air & Waste Management Association, vol. 44, Feb. 1994, pp. 169-175.

Paul Leonard Guenther, "Contributions to On-Road Remote Sensing of Automobile Exhaust," A Thesis Presented to the Faculty of Natural Sciences, Mathematics, and Engineering, University of Denver, Jun. 1992, 95 pages.

Donald H. Stedman, et al., "On-Road Remote Sensing of CO and HC Emissions in California," Prepared for Research Division, California Air Resources Board, Sacramento, CA, submitted by University of Denver Chemistry Department, Feb. 1994, 136 pages.

"Unstaffed On-Road Emissions Measurement Systems Services," Prepared by Parsons Engineering Science, Inc., Pasadena, California, Sep. 1995.

"Proposal/Quote for Unstaffed On-Road Emissions Measurement Systems Services" in response to Phase IV—RFQ #94/95-003, prepared by Remote Sensing Technologies, Inc. delivered to Department of Consumer Affairs, Bureau of Automotive Repair, Sacramento, California, Sep. 1, 1995.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Dec. 9, 1997, prepared by General Motors R&D Center, Michigan; 20 pages.

Steven H. Cadle, et al., "Measurement of Exhaust Particulate Matter Emissions from In-Use Light-Duty Motor Vehicles in the Denver, Colorado Area," Final Report, prepared for Coordinating Research Council, Atlanta, Georgia, Mar. 24, 1998, "Appendix E. University of Denver Remote Sensing Observation of Smoking Vehicles," prepared by General Motors R&D Center, Michigan; 20 pages.
Robert D. Stephens, et al., "Remote Sensing of Carbon Monoxide Emissions from On-Road Vehicles," Environmental Science Department, General Motors Research Laboratories, Michigan for presentation to Air and Waste Management Association, NC, May 1, 1990, 46 pages.
"Description and Documentation for Interim Vehicle Clean Screening Credit Utility," Draft Report, United States Environmental Protection Agency, May 1998, 40 pages.
David S. E. Petherick, "Ontario's Indoor, Controlled-Mode Remote Sensing I/M Prescreen Concept," Ministry of Transportation of Ontario, Copyright 1996 Society of Automotive Engineers, Inc., 9 pages.
P. A. Walsh, et al., "Texas 1996 Remote Sensing Feasibility Study," Final Report, prepared for Texas Natural Resource Conservation Commission, Austin, Texas, Aug. 29, 1997, prepared by Desert Research Institute, Energy and Environmental Engineering Center, Reno, Nevada, 9 pages.
"On Road Emissions Measurement System—Specifications," Bureau of Automotive Repair, Aug. 30, 1999, Revision—J, 15 pages.
Craig S. Rendahl, "Further Analysis of Wisconsin's Remote Vehicle Emissions Sensing Feasibility Studies," "Quality Control Efforts of Remote Vehicle Emissions Sensing," and "Data Handling and Validation from Wisconsin's Remote Vehicle Emissions Sensing Studies," Presented at the Air & Waste Management Annual Measurement of Toxics and Related Pollutants Conference, Research Triangle Park, North Carolina, May 1996, 34 pages.
James D. Peterson, et al., "Find and Fix the Polluters", Chemtech, Jan. 1992, Copyright 1992 American Chemical Society, 7 pages.
RSD 1000 Operator's Manual (Preliminary), Remote Sensing Technologies, IFB No. 94019, Jun. 1993, 66 pages.
RSD-1000 Remote Sensing Device Information Package to Mr. Wolf Klassen, Department of Natural Resources, Presented by Dennis L. Smith, Feb. 24, 1993, 123 pages.
Robert D. Stephens, et al., "An Experimental Evaluation of Remote Sensing-Based Hydrocarbon Measurements: A Comparison to FID Measurements", *Journal of the Air & Waste Management Association,* vol. 46, Feb. 1996, pp. 148-158.
Donald H. Stedman, "Automobile Carbon Monoxide Emission", *Environmental Science & Technology,* vol. 23, No. 2, 1989, pp. 147-149.
Masayuki Adachi, et al., "Automotive Emission Analyses Using FTIR Spectrophotometer", Published by the Society of Automotive Engineers, SAE# 920723, pp. 820-827.
Michael D. Koplow, et al., "Characterization of On-Road Vehicle NO Emissions by Means of a TILDAS Remote Sensing Instrument", Published by the Coordinating Research Council, Published for the 7th CRC On-Road Vehicle Emissions Workshop, Mar. 11, 1997, pp. 1-25.
Scott E. McLaren, et al., "Comparison of an Open Path UV and FTIR Spectrophotometer", Published by the Air & Waste Management Association, Published for Presentation at the 85th Annual Meeting & Exhibition, Kansas City, Missouri, Jun. 21-26, 1992, pp. 1-10.
"Developing an Inspection/Maintenance Program for Alternatively-Fueled Vehicles", Third Interim Report Submitted to the California Bureau of Automotive Repair, Submitted by Radian Corporation, Apr. 20, 1993, 147 pages.
Iain Frederick McVey, "Development of a Remote Sensor for Mobile Source Nitric Oxide", A Thesis Presented to the Faculty of Natural Sciences, Mathematics, and Engineering, University of Denver, Nov. 1992, 111 pages.
S. P. Beaton, et al., "Emission Characteristics of Mexico City Vehicles", *Journal of the Air & Waste Management Association,* vol. 42, No. 11, Nov. 1992, pp. 1424-1429.
Douglas R. Lawson, et al., "Emissions from In-Use Motor Vehicles in Los Angeles: A Pilot Study of Remote Sensing and the Inspection and Maintenance Program", *Journal of the Air & Waste Management Association,* vol. 40, No. 8, Aug. 1990, pp. 1096-1105.
Yi Zhang, et al., "Enhancement of Remote Sensing for Mobile Source Nitric Oxide", *Journal of the Air & Waste Management Association,* vol. 46, Jan. 1996, pp. 25-29.
Donald H. Stedman, et al., "Evaluation of a Remote Sensor for Mobile Source CO Emissions", U.S. Environmental Protection Agency, CR-815778-01-0, Report No. EPA/600/4-90/032, Jan. 1991, 90 pages.
James Butler, et al., "Factors Affecting the NDIR Measurement of Exhaust Hydrocarbons", Published by the Coordinating Research Council, Published for the CRC 5th On-Road Vehicle Emissions Workshop, 1995, 16 pages.
Scott E. McLaren, et al., "Flux Measurements Using Simultaneous Long Path Ultraviolet and Infrared Spectroscopy", Published by the Air & Waste Management Association, Published for Presentation at the 83rd Annual Meeting & Exhibition, Pittsburgh, Pennsylvania, Jun. 24-29, 1990, 7 pages.
Gary A. Bishop, et al., "Infrared Emission and Remote Sensing", *Journal of the Air & Waste Management Association,* vol. 42, No. 5, May 1992, pp. 695-697.
Hakan Axelsson, et al., "Measurement of Aromatic Hydrocarbons with the DOAS Technique", *Applied Spectroscopy,* vol. 49, No. 9, 1995, pp. 1254-1260.
Gary A. Bishop, et al., "Method Comparisons of Vehicle Emissions Measurements in the Fort McHenry and Tuscarora Mountain Tunnels", *Atmospheric Environment,* vol. 30, No. 12, 1996, pp. 2307-2316.
Donald H. Stedman, et al., "NOx Data by Remote Sensing", Published by the Coordinating Research Council, Published for the 5th CRC On-Road Vehicle Emissions Workshop, Apr. 3-5, 1995, 16 pages.
Donald H. Stedman, et al., "On-Road Carbon Monoxide and Hydrocarbon Remote Sensing in the Chicago Area", Final Report Prepared by University of Denver Chemistry Department, Prepared for Illinois Department of Energy and Natural Resources, Office of Research and Planning, Illinois Contract AQ 40, Project 91/122, Report No. ILENR/RE-AQ-91/14, Oct. 1991, pp. 1-70.
Gary A. Bishop, et al., "On-Road Carbon Monoxide Emission Measurement Comparisons for the 1988-1989 Colorado Oxy-Fuels Program", *Environmental Science & Technology,* vol. 24, No. 6, 1990, pp. 843-847.
Donald H. Stedman, et al., "On-Road CO Remote Sensing in the Los Angeles Basin", Final Report Prepared for the Research Division, California Air Resources Board, Submitted by University of Denver Chemistry Department, Aug. 1991, Contract No. A932-189, 70 pages.
Scott McLaren, "Open Path Spectrometers for Atmospheric Monitoring", A Dissertation Presented to the Faculty of Natural Sciences, Mathematics and Engineering, Nov. 1995, 170 pages.
Carol E. Lyons, et al., "Remote Sensing Enhanced Motor Vehicle Emissions Control for Pollution Reduction in the Chicago Metropolitan Area: Siting and Issue Analysis", Final Report Prepared by University of Denver Atmospheric Science Center, Prepared for Illinois Department of Energy and Natural Resources, Office of Research and Planning, Illinois Contract AQ 30, Project 90/009, Report No. ILENR/RE-AQ-91/15, Oct. 1991, pp. 1-65.
Peter John Popp, "Remote Sensing of Nitric Oxide Emissions from Planes, Trains and Automobiles", A Dissertation Presented to the Faculty of Natural Sciences, Mathematics and Engineering, Aug. 1999, 170 pages.
Brett C. Singer, et al., "Scaling of Infrared Remote Sensor Hydrocarbon Measurements for Motor Vehicle Emission Inventory Calculations", *Environmental Science & Technology,* vol. 32, No. 21, 1998, pp. 3241-3248.
Lucian W. Chaney, "The Remote Measurement of Traffic Generated Carbon Monoxide", *Journal of the Air Pollution Control Association,* vol. 33, No. 3, Mar. 1983, pp. 220-222.
Jose Luis Jimenez-Palacios, "Understanding and Quantifying Motor Vehicle Emissions with Vehicle Specific Power and TILDAS Remote Sensing", A Dissertation Presented to the Department of Mechanical Engineering, Feb. 1999, 360 pages.
"Vehicle Inspection Instrumentation", Published by the Lockheed Missiles and Space co., Inc., Report No. ARB-R-643-73-26, Jun. 30, 1973, 99 pages.

John E. Sigsby, Jr., et al., "Volatile Organic Compound Emissions from 46 In-Use Passenger Cars", *Environmental Science & Technology,* vol. 21, No. 5, 1987, pp. 466-475.
Yi Zhang, et at., "Worldwide On-Road Vehicle Exhaust Emissions Study by Remote Sensing", *Environmental Science & Technology,* vol. 29, No. 9, 1995, pp. 2286-2294.
Remote Sensing Technologies (RST), "RSD 1000", 1992.
Stationary Orem System, Small Hardened Environmental Pollution Sensor (SHEPS) for On-Road Emissions Measurements, Jun. 1995.
Remote Sensing Technologies (RST). "RSD 1000". 1992.

* cited by examiner

UNMANNED INTEGRATED OPTICAL REMOTE EMISSIONS SENSOR (RES) FOR MOTOR VEHICLES

Matter enclosed in heavy brackets [ ] appears in the original patent but forms no part of this reissue specification; matter printed in italics indicates the additions made by reissue.

*CROSS-REFERENCE TO* RELATED [APPLICATION] *APPLICATIONS*

This *application is a divisional reissue application of U.S. patent application Ser. No. 09/708,713, filed Nov. 9, 2000 (issued as U.S. Pat. No. Re. 40,767 on Jun. 23, 2009), which is a continuation of U.S. patent application Ser. No. 09/521,858, filed Mar. 9, 2000 (abandoned), which is a Reissue of U.S. patent application Ser. No. 08/739,487, filed Oct. 26, 1996 (which issued as U.S. Pat. No. 5,726,450 on Mar. 10, 1998). Additionally this* application is related to *U.S. patent* application Ser. No. 08/318,566, entitled "Optical Sensing Apparatus for Remotely Measuring Exhaust Gas Composition of Moving Motor Vehicles," filed Oct. 5, 1994, and [assigned to Santa Barbara Research Corporation, the assignee of the present invention] *issued as U.S. Pat. No. 5,591,975, issued Jan. 7, 1997.*

BACKGROUND OF THE INVENTION

1. Field of the Invention

This invention relates to the monitoring of environmental pollution, and more specifically to an unmanned integrated RES for remotely monitoring the exhaust gas composition of moving motor vehicles.

2. Description of the Related Art

Environmental pollution is a serious problem which is especially acute in urban areas. A major cause of this pollution is exhaust emissions from automotive vehicles. Official standards have been set for regulating the allowable amounts of pollutants species in automobile exhausts, and in some areas, periodic inspections or "smog checks" are required to ensure that vehicles meet these standards.

Anti-pollution devices which are required equipment on newer vehicles accomplish their intended purpose of reducing pollution in the vehicle exhaust to within prescribed levels. However, some older vehicles and special types of vehicles are exempt from inspections. Furthermore, some vehicle owners with mechanical expertise can perform whatever servicing is necessary to place their vehicles in condition to pass required inspections, and subsequently remove anti-pollution devices and/or return the vehicles with an attendant increase in pollutant emissions for normal use. The relatively small number of noncomplying vehicles generate a disproportionately large amount of pollution.

As a result, an anti-pollution program which depends entirely on mandatory periodic inspections performed at fixed facilities is inadequate. It is necessary to identify vehicles which are actually operating in violation of prescribed emission standards, and either require them to be placed in conformance with the standards or be removed from operation.

Manned RESs are now used to augment the periodic inspection program to identify vehicles that are in violation of the emissions standards. In general, RES are a nonobtrusive and cost-effective means for identifying the high pollution emitting vehicles and notifying the owner to take corrective action in a timely manner. The Smog Dog™ RES produced by Santa Barbara Research Center, the assignee of the present invention, includes a source and a receiver that are mounted on respective tripods and positioned on opposite sides of a road, a video camera and speed sensor that are mounted on a tripod that is positioned about 50 feet up the road in the direction of oncoming traffic, a van that contains a computer, data storage, power sources, calibration gas, and a video monitor, and a technician.

The source projects an IR beam across the road to the receiver which continuously senses pollutant levels such as carbon monoxide (CO), carbon dioxide ($CO_2$), hydrocarbons (HC), water ($H_2O$), nitric oxide ($NO_x$) in the received IR beam. When a vehicle passes through the IR beam, a sensor triggers the receiver to write the pollutant levels for the vehicle's exhaust plume to a data file in the data storage. The beam is set at a height to detect either low profile vehicles (cars) or high profile vehicles (trucks), but not both. The video camera takes a picture of the passing vehicle and the computer executes a character recognition program to identify the plate, which is then appended to the data file. If the speed sensor determines that the vehicle's acceleration and/or speed exceed certain levels, indicating that the vehicle's emissions control equipment are disabled, the recorded data is invalidated.

One drawback of the SMOG Dog™ and the other known RES systems is that the components, i.e. the sensor, receiver, video camera/speed sensor, and the van, are discrete parts that are positioned over a relatively large area. The source and receiver are positioned on opposite sides of the road. For safety purposes, they must be set back from the edges of the road. The video camera/speed sensor are positioned up the road such that their detection angles with respect to the passing vehicles is sufficiently shallow, approximately 3 degrees, to provide an accurate acceleration estimate and a high confidence of plate recognition. This can cause mismatch errors between the emissions readings and the plate recognition. Also, there must be enough room to park the van. These spatial requirements limit the applicability of the known RES systems. Furthermore, the discrete components are expensive because they require their own tripod, power supply, and alignment mechanisms.

Another drawback is that the known RES must be continuously manned by a technician, which is very expensive. After initial set up and alignment, the technician monitors the equipment to protect it from vandalism, performs required maintenance, and puts the system away at the end of the day. For example, the components may fall out of alignment due to the vibrations caused by passing vehicles, the various lenses may become occluded or the calibration gas may run out. Furthermore, the technician controls the data gathering process. The technician periodically places the RES in calibration mode, puffs a calibration gas into the IR beam to calibrate the system and evaluates the results displayed on the video monitor to accept or reject the calibration. Thereafter, the technician places the RES in data gathering mode, puffs the calibration gas, and compares the computed pollutant levels to the known levels of the calibration gas to accept or reject the verification of the calibration. During data gathering, the technician monitors both the signal levels of the exhaust plumes and the ambient air to determine whether the system has gone out of calibration or has a mechanical error. The technician also verifies the results of the plate recognition system.

U.S. Pat. No. 5,418,366 "IR-Based Nitric Oxide Sensor Having Water Vapor Compensation" issued May 23, 1995 discloses a specific receiver configuration having three channels for measuring a NO transmission, a water transmission, and a reference transmission, respectively, that are combined to give the effective NO transmission value. U.S. Pat. No. 5,210,702 "Apparatus for Remote Analysis of Vehicle Emissions" issued May 11, 1993 discloses a specific receiver configuration in which the ultraviolet beam is separated from the IR beam to sense the NO levels, and the IR beam is split into a plurality of components to measure CO, $CO_2$, HC and $H_2O$. Both systems use discrete source and receiver components placed on opposite sides of a road, a camera mounted on a tripod up the road, and a van for housing the control electronics, and require a technician to set the system up, calibrate the system, control the data gathering process, and pack it up at the end of the day.

In 1992 Remote Sensing Technologies (RST) experimented with a double-pass RES system called the RSD1000 in which a van housed both the source and the receiver and the video camera was suspended from a 20 foot boom. The IR beam was reflected off a mirror on the opposite side of the road back to the receiver. RST's system did not include the plate recognition or speed sensing capabilities, and never worked well enough for commercial exploitation. As a result, RST developed a one-pass system with the source and receiver on opposite sides of the road.

SUMMARY OF THE INVENTION

In view of the above problems, the present invention provides an unmanned integrated RES that reduces cost and simplifies operation.

This is accomplished by integrating each of the RES's components except the reflector into a single console that is positioned at the side of a road and providing a CPU that controls calibration, verification and data gathering. The source and receiver are preferably stacked one on top of the other such that the IR beam traverses a low and high path as it crosses the road. This allows the RES to detect both low and high ground clearance vehicles. To maintain the vehicle processing and identification throughput, the speed sensor and ALPR detect the passing vehicles at steep angles, approximately 20 to 35 degrees. In a preferred system, a manned control center communicates with a large number of the unmanned integrated RES to download emissions data, perform remote diagnostics, and if necessary, dispatch a technician to perform maintenance on a particular RES.

These and other features and advantages of the invention will be apparent to those skilled in the art from the following detailed description of preferred embodiments, taken together with the accompanying drawings, in which:

DETAILED DESCRIPTION OF THE INVENTION

The present invention provides an emissions sensing system that includes a plurality of unmanned integrated RES. A manned control center communicates with a large number of the RESs to download emissions data, perform remote diagnostics, and, if necessary, dispatch a technician to perform maintenance on a particular RES. The source, receiver, speed sensor, automated license plate reader (ALPR), gas canister, power supplies, and computer are integrated into a console that can be positioned at the side of a road either permanently or for an extended period of time. A reflector is positioned on the other side of the road to reflect the IR beam back to the receiver. The source and receiver are preferably stacked one on top of the other such that the IR beam traverses a low and high path as it crosses the road. This allows the RES to detect both low and high ground clearance vehicles. To maintain the vehicle processing and identification throughput of the known systems, the speed sensor and ALPR detect the passing vehicles at steep angles, approximately 20 to 35 degrees. This has the beneficial effect of reducing the number of mismatches between pollutant readings and vehicle identification. Furthermore, data gathering control including calibration, verification, and data gathering are automated. This eliminates the need for an on site technician, which further reduces cost.

Figure 1:
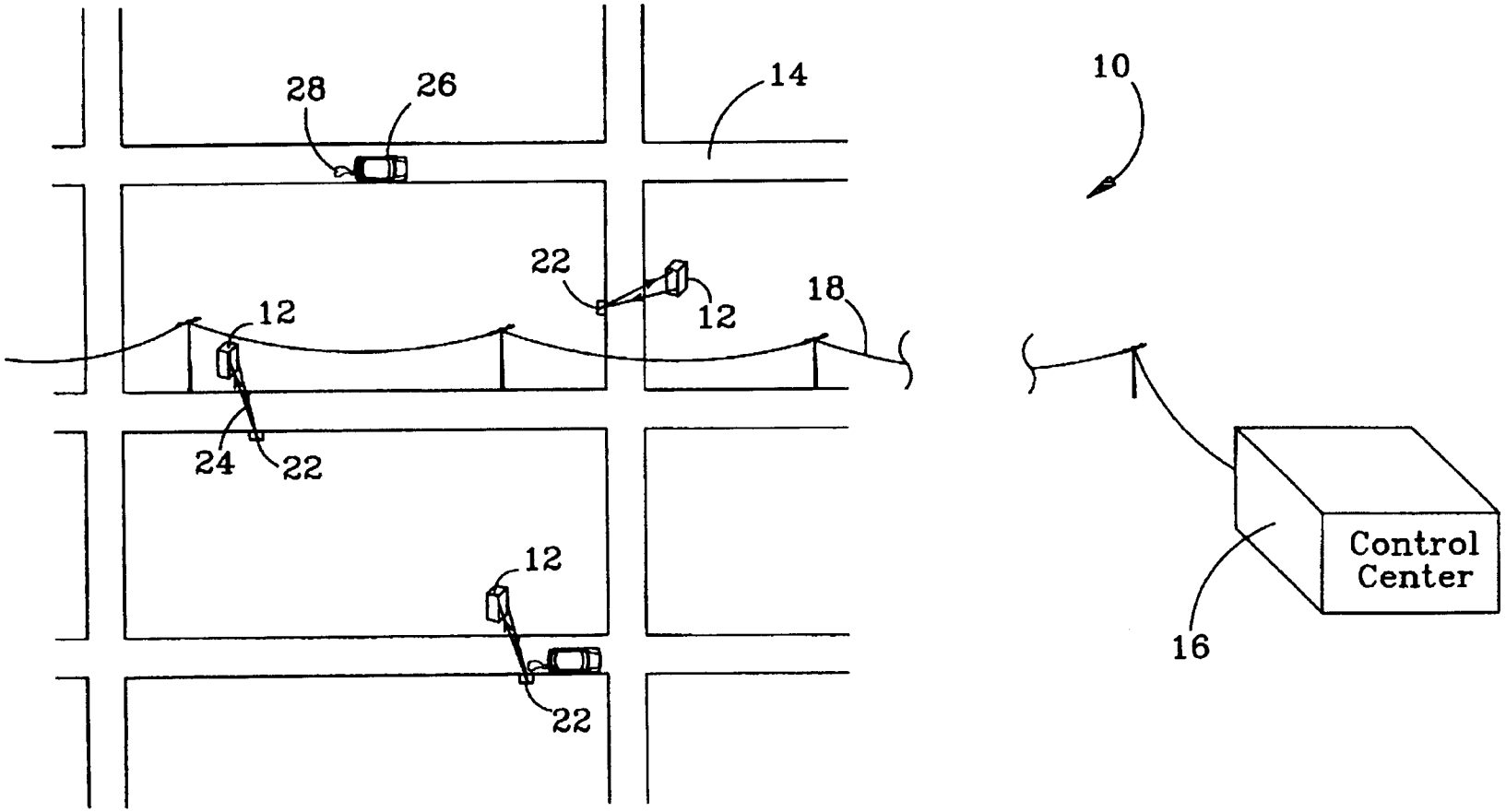
FIG. 1 is a diagram of an remote emissions sensing system in which a plurality of unmanned integrated RESs record vehicle emissions and communicate with a central unmanned control center.

As shown in FIG. 1, a remote emissions sensing system 10 includes a plurality of unmanned integrated RESs 12 that are placed at different positions in a network of roads 14, a manned control center 16 and a two-way communications channel 18. The communications channel shown is a wire-to-wire telephone network. Alternately, a cellular or satellite network could be used.

The RES 12 and a reflector 22 are placed on opposite sides of the road 14 and aligned such that the RES's IR beam 24 is reflected back to the RES 12. When a vehicle 26 passes through the IR beam 24, the RES 12 writes the pollutant levels from the vehicle's exhaust plume 28 to a data file and appends the vehicle's license plate number. If the vehicle's speed or acceleration are too high, indicating that the vehicle's emissions control have been disabled, the data is invalidated.

The RESs 12 are automated to maintain calibration and, if repeated recalibration fails, to notify the control center 16. The control center performs remote diagnostics to identify the cause of the calibration failure and, if possible, to correct the problem. Otherwise a technician is dispatched to the RES 12. The RESs 12 periodically download the gathered emissions data to the control center 16.

Figure 2:
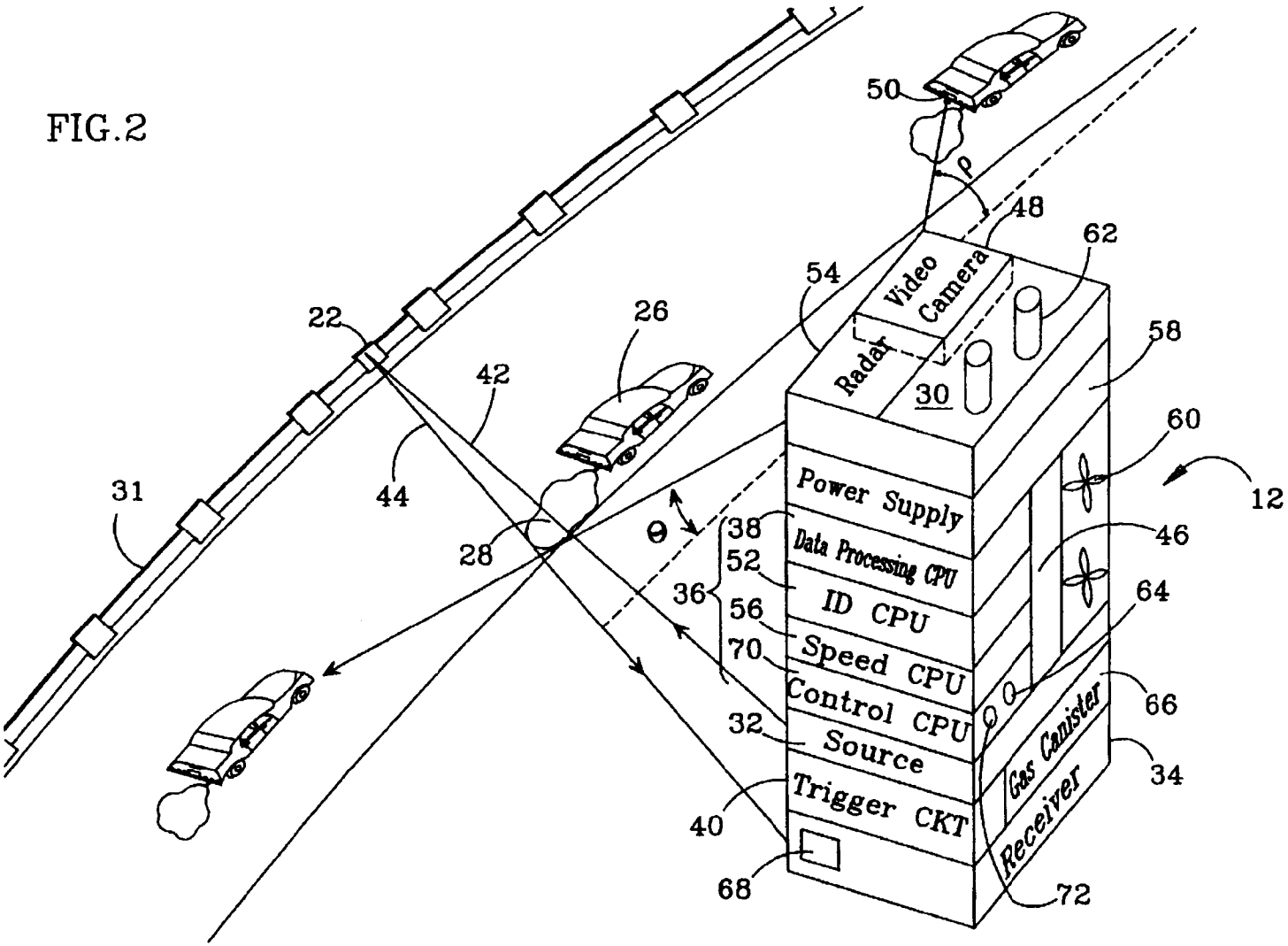
FIG. 2 is a perspective view of one of the unmanned integrated RESs shown in FIG. 1.

As shown in FIG. 2, all of the components of the RES 12, except for the reflector 22, are enclosed in a console 30, suitably 5' high, 3' wide, and 2' deep. The reflector 22 such as a piece of black aluminum that is opaque in the visible spectrum is attached to the guard rail at the side of the road, for example. A source 32 emits the IR beam 24 that crosses the road and reflects off of the reflector 22 back to a receiver 34. The receiver 34 samples the radiation levels in the beam 24 at various wavelengths. Because of the presence of NO, water vapor, $CO_2$, CO, HC and other molecular species within the exhaust plume 28, the IR beam 24 is partially absorbed at the various wavelengths when it passes through the plume. A computer 36 includes a data processing central processing unit (CPU) 38 that computes the composition of the ambient air, and when a vehicle passes by, computes the composition of the plume 28 in terms of the percentage or concentrations of the constituents NO, $CO_2$, CO and HC based on the sampled radiation levels. The computation of the composition is well known in the art and is thus omitted.

A trigger circuit 40 in the receiver 34 provides a trigger signal when a vehicle passes through the beam 24. The circuit responds to the sequential condition of the received signal going to zero, "beam block" followed by the received signal returning to a valid emissions level, "beam unblock." Placing the source 32 on top of the receiver 34 causes the IR beam 24 to traverse an upper path 42 across the road and to return along a lower path 44 to the receiver. As a result, the circuit will trigger on either low or high ground clearance vehicles. The trigger signal is fed to the data processing CPU 38 causing it to write the composition of the plume to a data file on a hard disk 46.

A vehicle identification system identifies the passing vehicle and appends the identification to the data file. The currently preferred approach is an automated license plate reader (ALPR) system that includes a video camera 48 that takes a picture of the vehicle's license plate 50 in response to the trigger signal and a identification CPU 52 that executes a character recognition algorithm to extract the plate number. Alternately, the vehicles could transmit identification codes that would be detected as the vehicles pass by the RES.

The video camera takes the picture at an angle ρ with respect to the road. The shallower the angle, the easier it is for the character recognition algorithm to extract the plate number. However, the shallower the angle, the farther the vehicle is past the RES when its plate is read. This increases the chance of mismatching the vehicle identification to the wrong data file. Furthermore, this reduces the number of vehicles that can be tested in a given time, i.e. the vehicle throughput.

Figure 6:
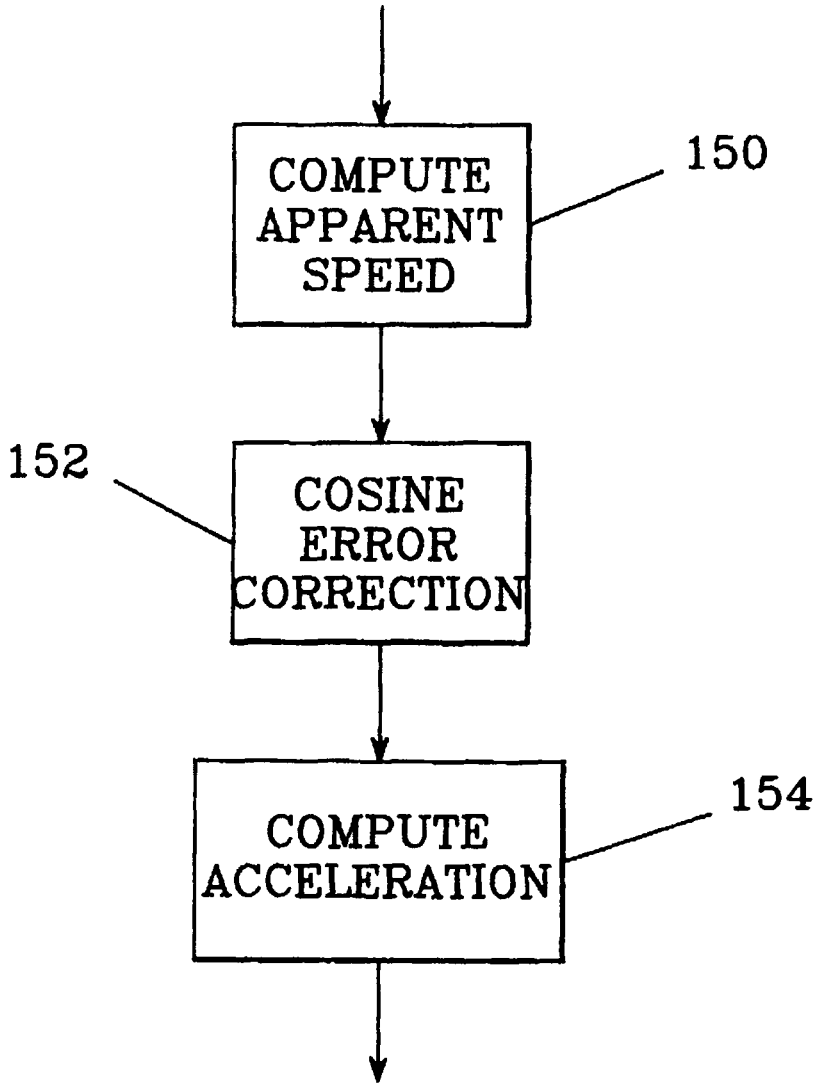
FIG. 6 is a flowchart illustrating the operation of the speed sensor shown in FIG. 2.
Figure 7:
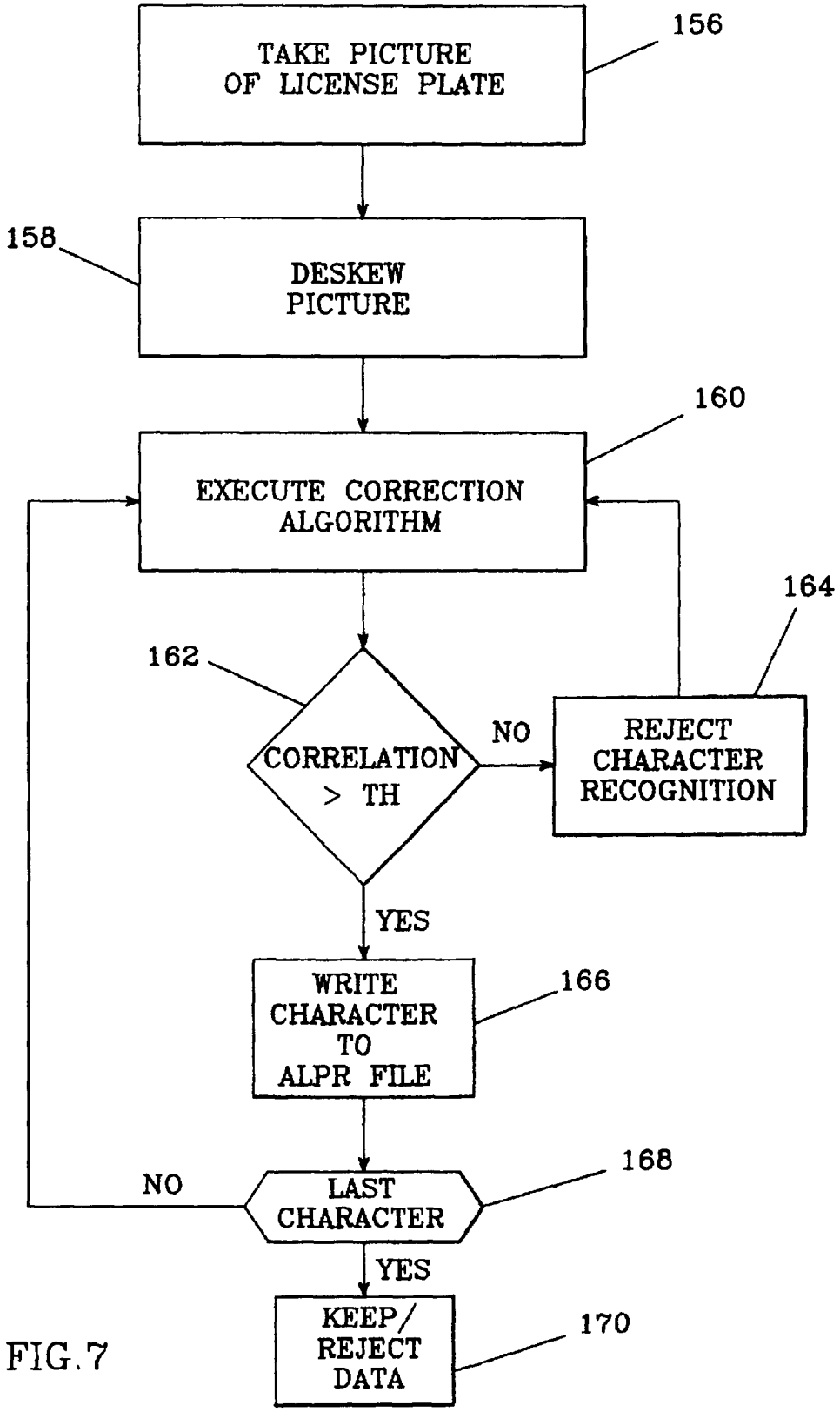
FIG. 7 is a flowchart illustrating the operation of the automated license plate reader (ALPR) shown in FIG. 2.

An optional speed sensor system determines the acceleration of an oncoming vehicle and invalidates the subsequently measured data if the acceleration is too high. The speed sensor system preferably includes an oblique angle radar 54 that detects oncoming vehicles and a CPU 56 that computes the vehicle's acceleration. Alternately, a LIDAR system, piezeo or pneumatic cables, or an optical sensor could be used to measure the vehicle's acceleration. Similar to the video camera, the slant radar detects the oncoming vehicle at an angle with respect to the road. The shallower the angle, the more accurate the estimate of the acceleration using known techniques but the lower the vehicle throughput. As a result, the known ALPR and speed/acceleration algorithms are modified as shown in FIGS. 7 and 6, respectively, to enable steep angle detection.

The RES 12 includes a number of secondary components that are required to support the data gathering process. A power supply 58 supplies power to the source 32, receiver 34, video camera 48, radar 54, and the CPUs. A pair of fans 60 cool the electrical systems in the RES 12. A pair of vents 62 vent the source and calibration gas to the atmosphere. An external computer port 64 allows a service technician to connect a laptop computer to the RES 12 to access the CPUs and perform diagnostics.

An automated control system controls the data gathering process for the RES 12. The primary function of the control system is to maintain calibration so that the recorded data is reliable. A gas canister 66 contains calibration gas that has a known composition of pollutants. When actuated, the gas canister 66 emits a puff of calibration gas in front of the source. This is used to both recompute the calibration curves and to verify the calibration.

The RES 12 can lose calibration for a number of reasons. First, the ambient conditions can change. For example, the $CO_2$ levels typically rise during the day, the HC levels near industrial plants will also rise during the day, heavy traffic will increase the background pollutant levels, and rain will destroy the IR signature. Second, mechanical problems such as the gas bottle being empty, the source being worn out, or a stolen reflector will result in a loss of calibration. Another common source of signal degradation is a dirty receiver lens. In known systems, when the technician notices signal degradation he manually cleans the lens on the receiver. In the automated RES, a multi-position lens cover 68 is placed in front of the receiver lens, and indexed when the signal levels degrade.

Figure 5:
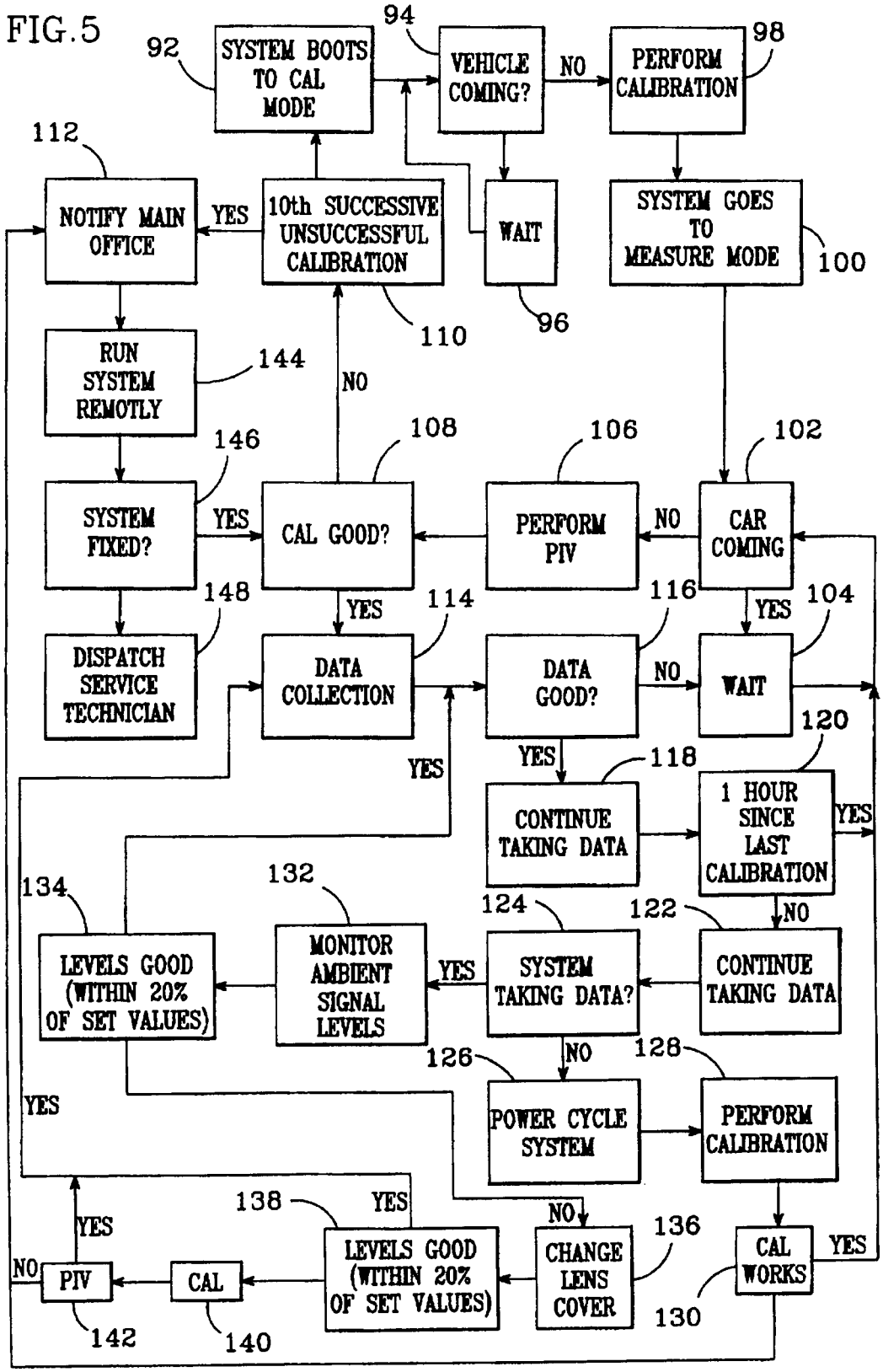
FIG. 5 is a block diagram of the automated control processes executed by the control CPU shown in FIG. 2.

A control CPU 70, as detailed in FIG. 5, automates the calibration, verification, and data gathering processes by controlling the actuation of the gas canister 66 and the indexing of the multi-position lens cover 68 and monitoring the compositions of the exhaust plume and ambient air. When repeated attempts to calibrate the system fail, the CPU 70 sends a help mess over the communications channel 18 shown in FIG. 1 via a communications port 72.

Figure 3:
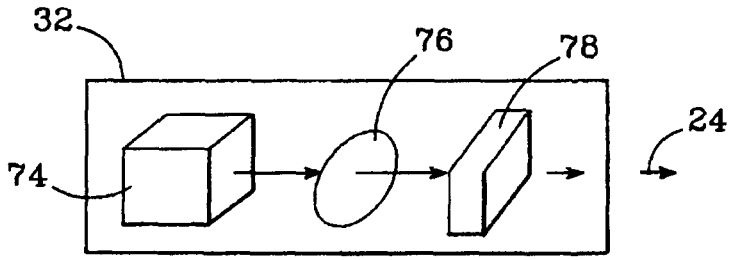
FIG. 3 is a diagram of the source shown in FIG. 2.

As shown in FIG. 3, the source 32 includes an IR source 74, preferably a broadband IR source such as a glow bar, that has a significant IR radiation output in the range of approximately 3 micrometers to approximately 6 micrometers. The IR source 74 provides a beam 24 that may optionally be passed through a chopper 76 (nominally 200 cycles per second) and a beam former 78, such as a parabolic reflector. In the preferred embodiment, the receiver 34 (shown in detail in FIG. 4) uses solid state detectors which must be turned on and off in order to detect the radiation levels. As a result, the chopper 76 is positioned in the path of the IR beam to block and unblock the beam and thereby switch the detectors on and off.

In the preferred embodiment, the chopper 76 is positioned at the IR source, which enables the system to distinguish infrared radiation emitted by the source from that emitted by the vehicle exhaust. When the chopper blocks the beam, the receiver measures the infrared radiation emitted from the plume. The data processing CPU calculates the peak-to-peak signal which removes the quiescent levels of the receiver as well as the interference from the vehicle exhaust. Thus, the measurements of the transmission levels are more accurate. Alternately, the chopper 76 can be positioned at the receiver. However, in this configuration the constituent measurements can be distorted by irradiance from the plume itself.

Figure 4:
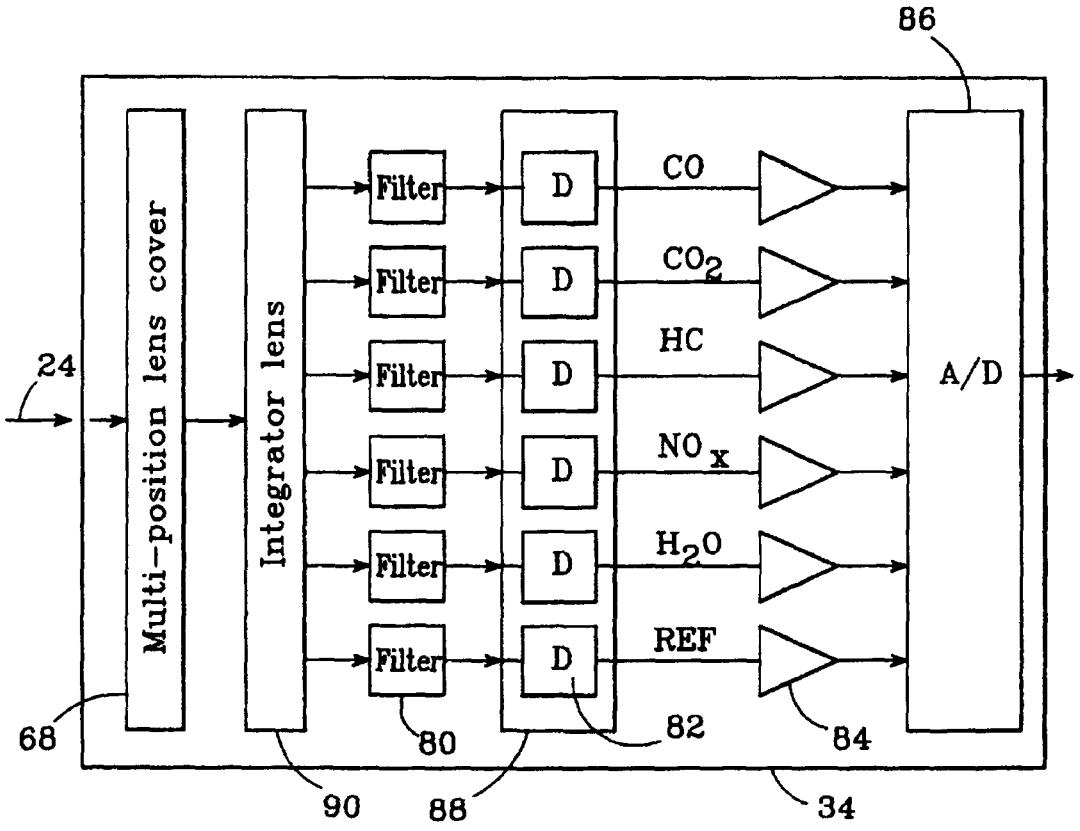
FIG. 4 is a diagram of the receiver shown in FIG. 2.

As shown in FIG. 4, the receiver 34 includes the multi-positioned lens cover 68 that is periodically indexed to provide a clean surface for receiving the IR beam 24. The multi-position lens cover 68 is preferably an IR transmissive sheet on a roller. The IR beam is applied to a plurality n of narrow band filters 80, where n is equal to a number of measurement channels. Each filter 80 is selected so as to pass a predetermined narrow band of wavelengths to an associated one of a plurality of IR detectors 82. The IR detectors include photosensitive elements which are integrally fabricated on a substrate. The elements are preferably photoconductive and formed of mercury cadmium telluride (HgCdTe or HCT), whereas the substrate is cadmium zinc telluride (CdZnTe).

Each detector 82 outputs an electrical signal corresponding to the radiation level at its wavelength to an amplifier 84. An n channel analog to digital (A/D) converter 86 digitizes the amplified signals and outputs them to the data processing CPU 38 shown in FIG. 2. A suitable cooler 88, such as a thermo-electric (TE) device, is employed for cooling those types of IR detectors 82 which are required to be cooled to an operating point that is below ambient temperature.

A beam integrator lens 90 is preferably placed between the lens cover 68 and the filters 80 to homogenize the beam 24 after propagation through the plume to remove the spatial and temporal variations of the constituent concentrations so that the detected signals are synchronized. The optical intensity or energy that is incident on the photodetectors 82 is substantially uniform throughout the cross-section of the homogenized beam 24. This ensures that the same homogenized or averaged scene is sensed by the photodetectors 82, and substantially increases the accuracy of the measurement by reducing the spatial and temporal variance of the constituent concentrations by over an order of a magnitude. The beam integrator lens enables synchronous operation of the photodetectors.

In a presently preferred embodiment of this invention there are six spectral measurement channels. These are an NO spectral channel (having a filter 80 with a passband centered on 5.26 μm), an $H_2O$ spectral channel (having a filter 80 with a passband centered on 5.02 μm), a first reference, or $CO_2$ spectral channel (having a filter 80 with a passband centered on 4.2 μm), a CO spectral channel (having a filter 80 with a passband centered on 4.6 μm), a HC spectral channel (having a filter 80 with a passband centered on 3.3 μm) and a second reference (REF) spectral channel (having a filter 80 with a passband centered on 3.8 μm). Additional channels to measure other pollutants can also be added if desired.

In general, the NO spectral channel is located near resonant absorption peaks in the vicinity of 5.2 μm; the water vapor spectral channel is in a region of strong water absorption where fundamental lines do not saturate; the first reference spectral channel is employed for normalizing the pollutants to the normal combustion products, i.e., $CO_2$; and the second reference (REF) spectral channel is provided at a region in which no atmospheric or automotive emissions gases absorb.

The REF spectral channel compensates the other five spectral channels for variations caused by: (a) fluctuations in the output of the IR source 74 shown in FIG. 3 during the passage of the vehicle; (b) particulate matter in the form of road dust; (c) particulate matter in the exhaust gas plume 28; (d) infrared radiation emitted from the exhaust plume, and any other factors that may reduce the amount of illumination reaching the detectors 82. The REF spectral channel thus operates to provide a baseline output which is independent of the molecular species (NO, $H_2O$, $CO_2$, CO and HC) being measured. The output of the second REF spectral channel is used to normalize, such as by dividing, the five molecular species spectral channels.

FIG. 5 is a flowchart of the automated control process executed by the control CPU 70 shown in FIG. 2 in cooperation with the manned control center 16 shown in FIG. 1. Once the RES is set up, the CPU 70 boots the system to a calibration mode (step 92) and uses the speed and acceleration data provided by the CPU 56 to determine whether a vehicle is approaching (step 94). If so, the CPU 70 waits (step 96) until no vehicles are in range and performs a calibration (step 98). The CPU 70 directs the gas canister to emit a puff of calibration gas so that the data processing CPU uses the radiation levels for the various pollutants and their known concentrations to recompute a set of calibration curves. Thereafter, the CPU 70 switches to a measurement mode (step 100).

Once in measurement mode, the CPU 70 again determines whether a vehicle is approaching (step 102), waits until no vehicle is in range (step 104), and performs a puff-in-vehicle (PIV) test (step 106) to verify the calibration. The CPU 70 directs the gas canister to emit another puff of calibration gas so that the data processing CPU uses the calibration curves to compute a composition for the calibration gas (step 108). If the composition deviates from a known reference composition of the calibration gas then the calibration is rejected. If calibration has failed repeatedly (step 110), for example 10 times in a row, the CPU 70 directs the RES to notify the control center (step 112). Otherwise the CPU 70 repeats steps 92 through 108 to recalibrate the system and verify the calibration.

When the composition calculated in step 108 is close enough to the reference composition, the calibration is accepted and data collection initiated (step 114). The data processing CPU will generate an error code 9999 when the data, i.e. the sensed radiation levels, is no good. Random and infrequent bad data is expected as part of the sensing process. However, a high percentage of bad data is indicative of a either a system problem such as an occluded lens, beam misalignment or mechanical problems in the source or the system being out of calibration. The CPU 70 monitors the data (step 116), and if the frequency of error codes exceeds a threshold, initiates recalibration by returning control to step 104. Otherwise, the data processing CPU continues gathering data (step 118).

Because the ambient conditions can change over time, the CPU 70 periodically verifies the last calibration (step 120) by returning control to step 102. The system continues gathering data (step 122) in the measurement mode while the CPU 70 monitors the data processing CPU to make sure that it is sampling the radiation levels and computing compositions (step 124). If not, the CPU 70 assumes that the system software has failed, power cycles the system (step 126) to reboot the software, performs a calibration (step 128), and determines whether the calibration was effective (step 130). If power cycling has restored the system, control returns to step 102 to verify the calibration. Otherwise, the CPU 70 causes the RES to notify the control center (step 112).

If the data processing CPU is receiving and processing the data in step 124, the CPU 70 monitors the ambient signal levels (radiation levels or compositions) (step 132). If the ambient signal levels are close enough to a set of reference values (step 134), for example, the values measured at the last calibration, then data gathering continues at step 114. If the signal levels have deviated, the CPU 70 indexes the lens cover 68 shown in FIG. 4 (step 136). Oftentimes signal deviation is due to dirt or exhaust building up on the lens of the receiver. Thereafter, the CPU 70 checks to determine whether the ambient signal levels have been corrected (step 138). If so, the data processing CPU continues gathering data (step 114). Otherwise, the CPU 70 performs a calibration (step 140) and a PIV (step 142). If the calibration is accepted, data gathering continues. If not, the RES notifies the control center (step 112).

When the RES notifies the control center (step 112), a technician at the control center executes remote diagnostics over the communications channel to identify the problem (step 144). If the system can be fixed remotely (step 146), control is returned to CPU 70 to gather data. Otherwise, a service technician is dispatched to the RES (step 148).

In order to maintain the same vehicle throughput as the known RES systems, the integrated RES radar 54 and video camera 48 shown in FIG. 2 must detect the approaching and passing vehicles, respectively, at a steep angle, approximately 20 to 35 degrees. As shown in FIG. 6, the CPU 56 computes the apparent speed measured by the radar 54 shown in FIG. 2 (step 150) and then corrects for what is called "cosine error" (step 152) by multiplying the apparent speed by the cosine of the detection angle (cos θ) to produce an accurate reading of the oncoming vehicle's true speed. In step 154, the CPU computes the vehicle's acceleration. The vehicle's speed and acceleration are used to determine whether the vehicle's emissions systems are disabled and can be used to predict when the vehicle should trigger data acquisition to reduce mismatch between recorded emissions and the identified license plate as detailed in FIG. 8.

As shown in FIG. 7, the preferred ALPR system deskews the picture of the vehicle's license plate to compensate for the steep detection angle prior to executing a character recognition algorithm. When triggered, the video camera 48 takes a picture of the passing vehicle's license plate at a steep angle (ρ), approximately 20 to 35 degrees (step 156). The system's CPU 52 (shown in FIG. 2) digitizes the picture into a digital image and transforms the skewed image into a normalized image, as if the picture had been taken at a shallow angle of approximately zero degrees (step 158). The steep-to-shallow angle transformation may be achieved using an affirm transformation, for example.

The CPU then executes a correlation algorithm on the first character in the normalized image to generate a correlation value for each character in an alpha-numeric set and selects the character with the highest correlation value (step 160). Thereafter, the correlation value of the selected character is compared to a recognition threshold. e.g. 90% (step 162). If the correlation value is less than the threshold, recognition is rejected (step 164). If the correlation value exceeds the threshold, the character is written into the ALPR file which is appended to the recorded emissions data file (step 166). The correlation algorithm is repeated for each character in the license plate until all the characters have been recognized or rejected (step 168). If only one or two of the characters in the license plate are rejected, the plate may still be uniquely identifiable. If so, the partial plate can be appended to the emissions data and recorded. However, if too many characters in the entire license plate are rejected, then the entire plate recognition is rejected and the recorded emissions data is not reported (step 170).

Figure 8:
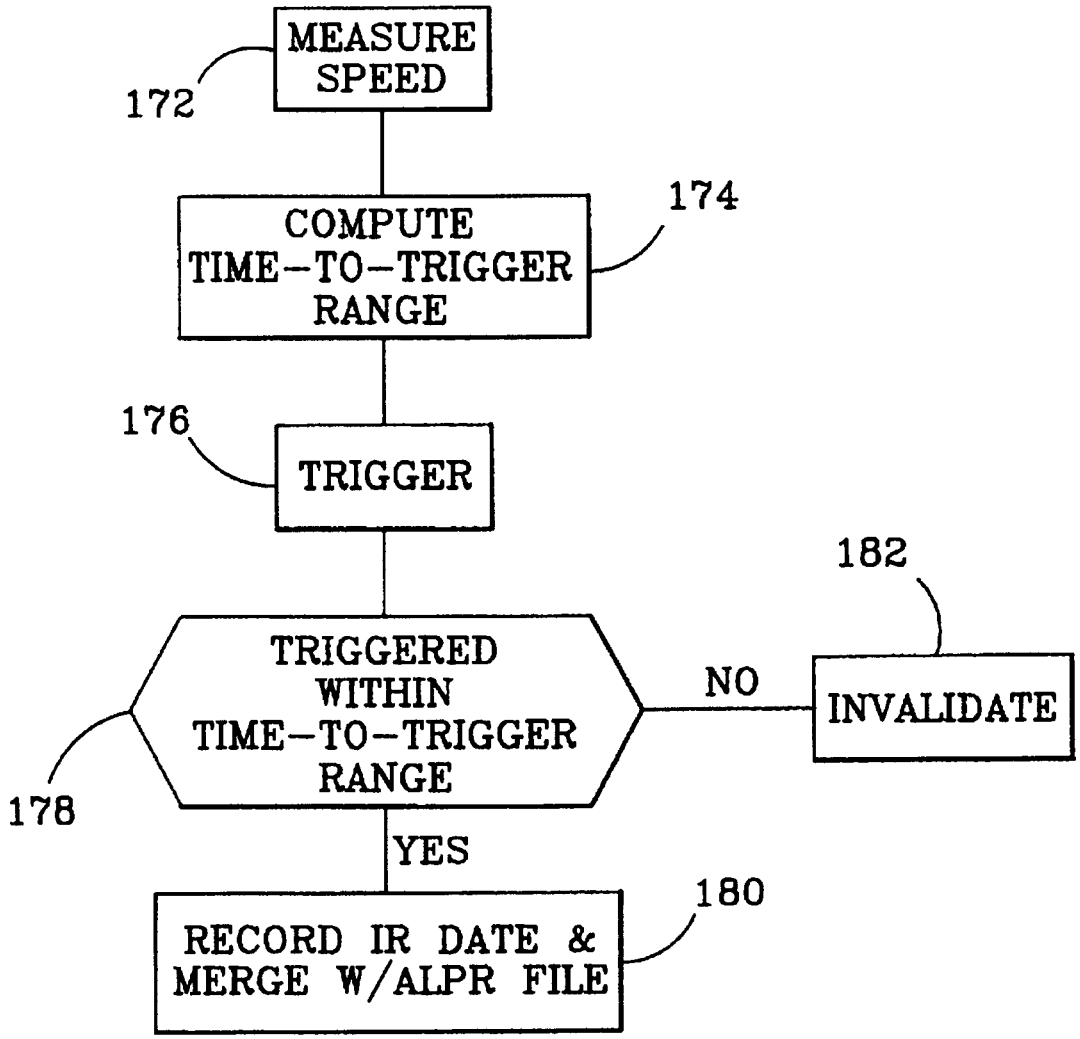
FIG. 8 is a flowchart illustrating the coordination of the speed sensor and the ALPR shown in FIG. 2.

A common problem in known RES systems is a mismatch between the recorded emissions data and the license plate, i.e. the wrong car is matched to the offending emissions. The steep angles used by the radar and video camera reduce the frequency of mismatches to some extent by confining the area in which they look for a passing vehicle. As illustrated in FIG. 8, the mismatch frequency can be further reduced by combining the speed and acceleration information provided by the radar with the trigger signal. In step 172, the data processing CPU computes the speed and acceleration of an approaching vehicle as described in FIG. 6. The CPU uses this information and the distance to the vehicle to estimate a time-to-trigger range(step 174). When the vehicle passes through the IR beam, the CPU records the trigger time (step 176) and determines whether it falls within the time-to-trigger range (step 178). If the trigger falls within the range, the CPU merges the emissions data with the license plates (step 180). Otherwise, the CPU invalidates the data (step 182).

While several illustrative embodiments of the invention have been shown and described, numerous variations and alternate embodiments will occur to those skilled in the art. Such variations and alternate embodiments are contemplated, and can be made without departing from the spirit and scope of the invention as defined in the appended claims.

We claim:

[1. An unmanned optical emissions sensor for sensing a gas mixture composition of an exhaust plume of a motor vehicle travelling along a road, comprising:

a source for radiating a beam of light along a path across a road such that the beam passes through the exhaust plume of a passing vehicle and otherwise passes through ambient air;

a receiver for sampling radiation levels at a plurality of predetermined wavelengths from the beam;

a canister for emitting a puff of calibration gas in the path of the beam between the source and the receiver, said calibration gas having a known reference composition at the predetermined wavelengths;

a data processing computer for computing a gas mixture composition from the sensed radiation levels in accordance with stored calibration curves;

a trigger device that produces a trigger signal when a vehicle passes through the beam causing the data processing computer to record the gas mixture composition of the vehicle's exhaust plume for a period of time;

an automated control computer that a) calibrates the data processing computer by directing the canister to emit a puff of calibration gas, whereby the data processing computer recomputes the calibration curves in accordance with the known reference composition;

b) verifies the calibration by directing the canister to emit a puff of calibration gas, whereby the data processing computer computes a test composition from the radiation levels and accepts the calibration when the test composition is close enough to the known reference composition and otherwise rejects the calibration and initiates recalibration; and c) monitors the gas mixture composition of the ambient air to control recalibration of the data processing computer; and a vehicle identification device that responds to the trigger signal by recording a vehicle identification for the passing vehicle.]

[2. The unmanned optical emissions sensor of claim 1, further comprising:

a multi-position lens cover on the receiver, said automated control computer indexing the position of the lens cover when the gas mixture composition of the ambient air deviates from an ambient reference level by more than a specified threshold and initiates recalibration if the deviation remains greater than the specified threshold.]

[3. The unmanned optical emissions sensor of claim 1, wherein the automated control computer monitors the gas mixture composition of the vehicle's exhaust plume to control reverification of the calibration.]

[4. The unmanned optical emissions sensor of claim 1, wherein the automated control computer monitors a time from the last calibration and when the time exceeds a mandatory recalibration period it initiates another calibration.]

[5. The unmanned optical emissions sensor of claim 1, wherein the automated control computer monitors the data processing computer and power cycles the emissions sensor when the data processing computer fails to produce gas mixture compositions.]

[6. The unmanned optical emissions sensor of claim 1, further comprising:

a manned control center; and a communications channel for communication between the automated control computer and the manned control center, said automated control computer responding to repeated calibration rejections by transmitting a help message to the manned control center, which in turn responds by performing diagnostics to determine a cause for the calibration rejection and then either remedy the cause remotely or dispatch a technician to remedy the cause on site.]

[7. The unmanned optical emissions sensor of claim 1, further comprising:

a vehicle detector for sensing an oncoming vehicle and computing its acceleration, said data processing computer disabling the recordation of the composition of the vehicle's exhaust plume when the acceleration exceeds a threshold.]

[8. The unmanned optical emissions sensor of claim 7, wherein the vehicle detector compute's the vehicle's speed and computes a time-to-trigger range from the vehicle's measured speed and acceleration, said data processing computer disabling the recordation of the composition of the vehicle's exhaust plume when triggering occurs outside the time-to-trigger range.]

[9. The unmanned optical emissions sensor of claim 7, wherein said source and said receiver are placed on the same side of the road, further comprising:

a reflector that is positioned on the other side of the road such that the beam emitted by the source reflects off of the reflector and back to the receiver.]

[10. The unmanned optical emissions sensor of claim 9, further comprising:

a single console that contains the source, the receiver, the canister, the data processing computer, the automated control computer, the vehicle identification device, and the vehicle detector.]

[11. The unmanned optical emissions sensor of claim 10, wherein the vehicle identification device comprises an automated license plate reader (ALPR) that reads the vehicle's license at an angle of at least 20 degrees and said vehicle detector senses the oncoming vehicle at an angle of at least 20 degrees to maintain a vehicle throughput.]

[12. The unmanned optical emissions sensor of claim 10, wherein one of said source and said receiver is positioned above the other so that the beam traverses the road in a low path in one direction and in a high path in the other direction so that the trigger device will trigger on both high and low ground clearance vehicles.]

[13. An integrated optical emissions sensor for sensing a gas mixture composition of an exhaust plume of a motor vehicle travelling along a road, comprising:

a single console that is positioned at one side of the road;

a vehicle detector in said console for sensing an oncoming vehicle and computing its acceleration;

a source in said console for radiating a beam of light along a path across the road such that the beam passes through the exhaust plume of a passing vehicle and otherwise passes through ambient air;

a reflector that is positioned on the other side of the road such that the beam reflects off of the reflector and back to the console;

a receiver in said console sampling radiation levels at a plurality of predetermined wavelengths from the beam;

a data processing computer in said console for computing a gas mixture composition from the sensed radiation levels in accordance with stored calibration curves;

a canister in said console for emitting a puff of calibration gas in the path of the beam between the source and the receiver to recompute the calibration curves;

a trigger device in said console that produces a trigger signal when a vehicle passes through the beam causing the data processing computer to record the gas mixture composition of the vehicle's exhaust plume for a period of time, said data processing computer disabling the recordation of the composition of the vehicle's exhaust plume when the acceleration exceeds a threshold; and a vehicle identification device in said console that responds to the trigger signal by recording a vehicle identification for the passing vehicle.]

[14. The unmanned optical emissions sensor of claim 13, wherein the vehicle identification device comprises an automated license plate reader (ALPR) that reads the vehicle's license at an angle of at least 20 degrees and said vehicle detector senses the oncoming vehicle at an angle of at least 20 degrees to maintain a vehicle throughput.]

[15. The unmanned optical emissions sensor of claim 13, wherein one of said source and said receiver is positioned above the other so that the beam traverses the road in a low path in one direction and in a high path in the other direction so that the trigger device will trigger on both high and low ground clearance vehicles.]

[16. The unmanned optical emissions sensor of claim 13, wherein the vehicle detector compute's the vehicle's speed and computes a time-to-trigger range from the vehicle's measured speed and acceleration, said data processing computer disabling the recordation of the composition of the vehicle's exhaust plume when triggering occurs outside the time-to-trigger range.]

[17. The unmanned optical emissions sensor of claim 13, wherein said calibration gas has a known reference composition at the predetermined wavelengths, further comprising an automated control computer that a) calibrates the data processing computer by directing the canister to emit a puff of calibration gas, whereby the data processing computer recomputes the calibration curves in accordance with the known reference composition;

b) verifies the calibration by directing the canister to emit a puff of calibration gas, whereby the data processing computer computes a test composition from the radiation levels and accepts the calibration when the test composition is close enough to the known reference composition and otherwise rejects the calibration and initiates recalibration; and c) monitors the gas mixture composition of the ambient air to control recalibration of the data processing computer.]

[18. A remote emissions sensing system sensing gas mixture compositions of exhaust plumes for motor vehicles traveling along a network of roads, comprising:

a plurality of unmanned integrated optical emissions sensors positioned at different places in the network on a side of the road, each emissions sensor comprising:

a console;

a vehicle detector in said console for sensing an oncoming vehicle and computing its acceleration;

a source in said console for radiating a beam of light along a path across the road such that the beam passes through the exhaust plume of a passing vehicle and otherwise passes through ambient air;

a reflector that is positioned on the other side of the road such that the beam reflects off of the reflector and back to the console;

a receiver in said console that samples radiation levels at a plurality of predetermined wavelengths from the beam;

a data processing computer in said console for computing a gas mixture composition from the sensed radiation levels in accordance with stored calibration curves;

a canister in said console for emitting a puff of calibration gas in the path of the beam between the source and the receiver, said calibration gas having a known reference composition at the predetermined wavelengths;

a trigger device in said console that produces a trigger signal when a vehicle passes through the beam causing the data processing computer to record the gas mixture composition of the vehicle's exhaust plume for a period of time, said data processing computer invalidating the recordation of the composition of the vehicle's exhaust plume when the acceleration exceeds a threshold;

an automated control computer that a) calibrates the data processing computer by directing the canister to emit a puff of calibration gas, whereby the data processing computer recomputes the calibration curves in accordance with the known reference composition;

b) verifies the calibration by directing the canister to emit a puff of calibration gas, whereby the data processing computer computes a test composition from the radiation levels and accepts the calibration when the test composition is close enough to the known reference composition and otherwise rejects the calibration and initiates recalibration; and c) monitors the gas mixture composition of the ambient air to control recalibration of the data processing computer; and a vehicle identification device in said console that responds to the trigger signal by recording a vehicle identification for the passing vehicle;

a manned control center; and a communications channel for communication between the emissions sensors and the manned control center, said emissions sensors responding to repeated calibration rejections by transmitting a help message to the manned control center, which in turn responds by performing diagnostics to determine a cause for the calibration rejection and then either remedy the cause remotely or dispatch a technician to remedy the cause on site.]

[19. The unmanned optical emissions sensor of claim 18, wherein the vehicle detector compute's the vehicle's speed and computes a time-to-trigger range from the vehicle's measured speed and acceleration, said data processing computer disabling the recordation of the composition of the vehicle's exhaust plume when triggering occurs outside the time-to-trigger range.]

[20. The unmanned optical emissions sensor of claim 18, wherein the vehicle identification device comprises an automated license plate reader (ALPR) that reads the vehicle's license at an angle of at least 20 degrees and said vehicle detector senses the oncoming vehicle at an angle of at least 20 degrees to maintain a vehicle throughput.]

[21. The unmanned optical emissions sensor of claim 18, wherein one of said source and said receiver is positioned above the other so that the beam traverses the road in a low path in one direction and in a high path in the other direction so that the trigger device will trigger on both high and low ground clearance vehicles.]

*22. A system for monitoring emissions of moving motor vehicles comprising:*

*a plurality of remote emissions sensing devices deployed at a plurality of testing locations, said sensing devices automatically gathering emissions data on a plurality of moving vehicles; and*

*a central control, said central control connected to each of said plurality of remote emissions sensing devices via a communications channel, said central control receiving emissions data on the plurality of moving vehicles and performing remote diagnostics on said plurality of remote emissions sensing devices.*

*23. A method of monitoring vehicle emissions comprising:*

*gathering emissions data on moving motor vehicles at a plurality of testing locations using a plurality of remote emissions sensing devices;*

*downloading emissions data gathered by the remote emissions sensing devices to a central control; and*

*performing remote diagnostic checks of the remote emissions sensing devices from the central control.*

*24. The method of claim 23, wherein the step of performing remote diagnostic checks comprises remotely initiating repeated calibration attempts and analyzing returned data.*

*25. The method of claim 23, wherein the step of performing remote diagnostic checks comprises remote actuation of a mechanical part of at least one of the remote emission sensing devices.*

*26. The method of claim 25, wherein the mechanical part is a receiver lens cover.*

*27. A system for monitoring emissions of moving motor vehicles, comprising:*

*a first remote emissions sensing device deployed at a first testing location, the first remote emissions sensing device configured to gather emissions data from one or more moving motor vehicles driving past the first testing location;*

*a second remote emissions sensing device deployed at a second testing location that is located remotely from the first testing location, the second remote emissions sensing device configured to gather emissions data from one or more moving motor vehicles driving past the second testing location; and*

*a control center, located remotely from the first testing location and the second testing location, the control center in operative communication with the first remote emissions sensing device and the second remote emissions sensing device, and configured to:*

*(1) receive gathered emissions data from the first remote emissions sensing device and the second remote emissions sensing device; and*

*(2) perform remote diagnostics on the first remote emissions sensing device and the second remote emissions sensing device.*

*28. A method of monitoring emissions of moving motor vehicles, comprising:*

*receiving, at a control center, from a first remote emissions sensing device in operative communication with the control center and located remotely from the control center, emissions data gathered by the first remote emissions sensing device corresponding to one or more moving motor vehicles that drive past the first remote emissions sensing device;*

*receiving, at the control center, from a second remote emissions sensing device in operative communication with the control center and located remotely from the control center, emissions data gathered by the second remote emissions sensing device corresponding to one or more moving motor vehicles that drive past the second remote emissions sensing device, wherein the second remote emissions sensing device is located remotely from the first remote emissions sensing device; and*

*performing remote diagnostic checks of the first remote emissions sensing device and the second remote emissions sensing device from the control center.*

* * * * *